United States Patent [19]

Miyashita

[11] Patent Number: 4,841,096
[45] Date of Patent: Jun. 20, 1989

[54] CYCLOHEXANE-2,5-DIONE-1,4-YLENE-BIS (-3-PROPIONIC ACID) DERIVATIVES AND PROCESS FOR PREPARING THE SAME

[75] Inventor: Masahiko Miyashita, Osaka, Japan

[73] Assignee: Nippon Gosei Kaagaku Kogyo, Japan

[21] Appl. No.: 129,982

[22] Filed: Dec. 8, 1987

Related U.S. Application Data

[63] Continuation-in-part of Ser. No. 835,531, Mar. 3, 1986, abandoned, and a continuation-in-part of Ser. No. 878,199, Jun. 25, 1986, Pat. No. 4,772,432.

[30] Foreign Application Priority Data

Mar. 5, 1985 [JP]  Japan .................................. 60-43019
Jul. 27, 1985 [JP]  Japan ................................ 60-166081

[51] Int. Cl.$^4$ ............................................. C07C 69/75
[52] U.S. Cl. ..................................... 560/126; 562/528
[58] Field of Search ......................... 560/126; 562/508

[56] References Cited

U.S. PATENT DOCUMENTS 3,024,268  3/1962  Struve ................................. 560/126

OTHER PUBLICATIONS

Chang, Chem. Abstr., 50: 7725g (1956).
Chang, Chem. Abstr., 55: 133356 (1961).

*Primary Examiner*—Michael L. Shippen

*Attorney, Agent, or Firm*—McGlew & Tuttle

[57] ABSTRACT

A cyclohexane-2,5-dione-1,4-ylene-bis (-3-propionic acid) derivative represented by the formula

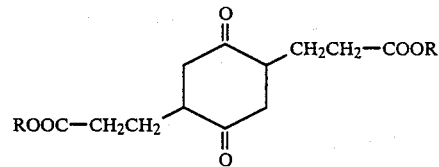

wherein R is hydrogen or alkyl. The derivative is prepared by heating a cyclohexane-2,5-dione derivative represented by the formula

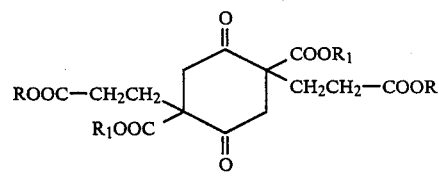

wherein R is as defined above, and $R_1$ is alkyl, in the presence of water.

5 Claims, No Drawings

CYCLOHEXANE-2,5-DIONE-1,4-YLENE-BIS (-3-PROPIONIC ACID) DERIVATIVES AND PROCESS FOR PREPARING THE SAME

CROSS REFERENCE TO RELATED APPLICATION

This is a continuation-in-part of copending U.S. applications Ser. No. 835,531 filed Mar. 3, 1986, and Ser. No. 878,199 filed June 25, 1986 U.S. Pat. No. 4,772,432.

FIELD AND BACKGROUND OF THE INVENTION

The present invention provides novel compounds which are useful as materials for producing polyesters, polyamides, polyurethanes, etc. and also as intermediates for tetracyanoquinodimethanes (TCNQ).

SUMMARY OF THE INVENTION

The compounds of the invention are represented by the following formula

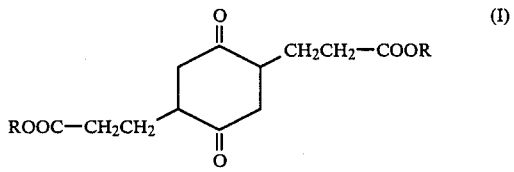

wherein R is hydrogen or alkyl, and are not disclosed in literature. The present compound is prepared by heating a cyclohexane-2,5-dione derivative represented by the formula

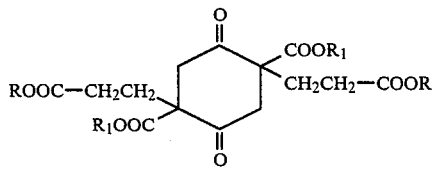

wherein R is hydrogen or alkyl, and $R_1$ is alkyl, in the presence of water, or water and a strong acid.

The cyclohexane-2,5-dione derivative is also a novel compound which is obtained by reacting a dialkyl succinylsuccinate with acrylic acid or with an alkyl acrylate.

DESCRIPTION OF THE PREFERRED EMBODIMENTS

The process of the present invention is represented by the following reaction scheme:

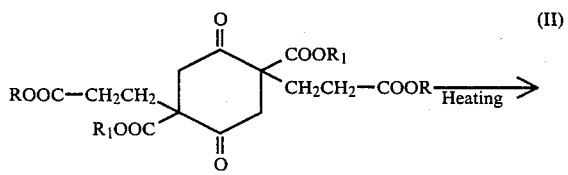

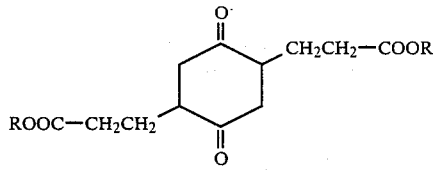

wherein R is hydrogen or alkyl, and $R_1$ is alkyl.

Examples of alkyl groups for each R individually, and each $R_1$ individually, are those having 1 to about 10 carbon atoms, such as methyl, ethyl, propyl, butyl, amyl, hexyl, octyl, decyl, cyclohexyl, etc., especially lower alkyl groups having 1 to about 4 carbon atoms, and particularly methyl and ethyl.

The reaction is conducted in the presence of water, which must be used in an amount of at least two moles per mole of the cyclohexane-2,5-dione derivative. Water may be used in a large amount generally suited for use as a solvent. When a relatively small amount of water is used, a high-boiling solvent such as polyethylene glycol may be used. It is advantageous to continue the reaction while distilling off the alcohol produced as a by-product during the reaction. A satisfactory result can be achieved by conducting the reaction with heating (preferably from refluxing temperature to 150° C.) at atmospheric or increased pressure for about 1 to about 150 hours.

The reaction may be conducted further in the presence of a strong acid. Examples of preferred strong acids are hydrochloric acid, sulfuric acid, p-toluene-sulfonic acid, strong acid-type ion exchange resin, etc. The acid is used in an amount of about 20 to about 200% by weight based on the starting material, i.e., cyclohexane-2,5-dione derivative.

After the completion of the reaction, the remaining by-product alcohol is distilled off, and the reaction mixture is cooled, whereby the desired product is separated out. The product is filtered off in the usual manner.

When required, the product is purified, for example, by recrystallization.

The cyclohexane-2,5-dione-1,4-ylene-bis(-3-propionic acid) obtained is in the form of a mixture of trans-form (crystalline) and cis-form (oily) and can be used usually in this form for various applications. When required, one form may be separated from the other.

While the process described above affords the compound of the invention in the form of a free acid, the acid can be esterified for the contemplated use. The compound, i.e., cyclohexane-2,5-dione-1,4-ylene-bis(-3-propionic acid), is esterified by a known method, for example, by converting the acid into an acid chloride with use of thionyl chloride or the like and reacting the acid chloride with an alcohol. Examples of useful alcohols are those having about 1 to about 10 carbon atoms, such as methanol, ethanol, propanol, butanol, amyl alcohol, hexyl alcohol and octyl alcohol.

The various compounds of the present invention are useful as materials for producing polyesters, polyamides, polyurethanes, etc. or as intermediates for tetracyanoquinodimethanes (TCNQ) which are useful as organic semiconductors.

Polyesters can be produced by subjecting the compound of the present invention, a polycarboxylic acid, such as phthalic acid, isophthalic acid, maleic acid or maleic anhydride, and a polyhydric alcohol, such as ethylene glycol or propylene glycol, to a condensation reaction. Polyamides can be prepared by subjecting the present compound, a polycarboxylic acid such as adipic acid, and a polyamine compound such as ethylenediamine to a condensation reaction. Polyurethanes can be prepared by reacting the present compound with a polyhydric alcohol such as ethylene glycol, polyesterpolyol and a polyisocyanate compound such as tolylene diisocyanate or diphenylmethane diisocyanate.

Tetracyanoquinodimethanes can be prepared by subjecting malononitrile and the present compound to a condensation reaction to obtain the corresponding 1,4-bis(dicyanomethylene)cyclohexane derivative, and oxidizing said cyclohexane derivative in pyridine with N-bromosuccinimide or bromine.

Thus, the present invention provides novel compounds which are useful as materials for producing polyesters, polyamides, polyurethanes, etc. and as intermediates for tetracyanoquinodimethanes serving as organic semiconductors, and which can be prepared by the methods as discussed hereinabove.

It will be appreciated that said copending Ser. No. 878,199 discloses and claims 7,7,8,8-tetracyanoquinodimethane-2,5-ylene-(3-propionic acid) and derivatives thereof represented by the formula

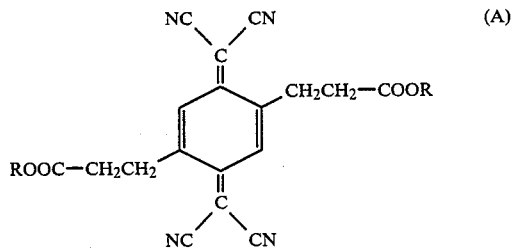

wherein each R individually is hydrogen or alkyl.

Examples of alkyl groups for each R individually in formula (A) are those having 1 to about 10 carbon atoms, such as methyl, ethyl, propyl, butyl, amyl, hexyl, octyl, decyl, cyclohexyl, etc. Important from an industrial viewpoint are lower alkyl groups having 1 to about 4 carbon atoms, especially methyl. When both R moieties of formula (A) are methyl, the compound has a melting point of as low as 168° C. and is satisfactorily soluble in common solvents such as methanol, and therefore has the advantage of being usable for wider applications.

The compound of formula (A) is prepared by oxidizing 2,5-bis(dicyanomethylene)cyclohexane-1,4-ylene-(propionic acid) or a derivative thereof represented by the formula

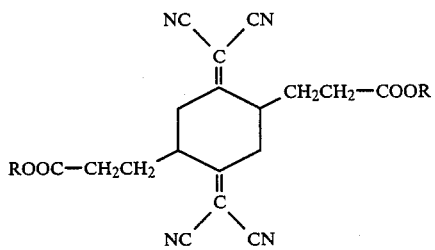

wherein each R individually is hydrogen or alkyl as aforesaid.

The oxidation reaction is conducted in an inert gas atmosphere using N-bromosuccinimide or bromine, usually in acetonitrile or other medium in the presence of pyridine or other basic substance. Satisfactory results can be achieved when the reaction is carried out at 0° to 80° C. for 0.1 to 8 hours.

N-bromosuccinimide or bromine is reacted with 2,5-bis(dicyanomethylene)cyclohexane-1,4-ylene-(3-propionic acid) or a derivative thereof represented by the formula (B) usually in the ratio of 1 to 5 moles of the former per mole of the latter. After completion of the reaction, water is added to the reaction mixture as required to separate out a precipitate, which is then purified by the usual method.

When the 2,5-bis(dicyanomethylene)cyclohexane-1,4-ylene-(3-propionic acid) of formula (B) is used as the starting material, 7,7,8,8-tetracyanoquinodimethane-2,5-ylene-(3-propionic acid) is obtained. When the starting material used is an alkyl ester of the 2,5-bis(dicyanomethylene)cyclohexane-1,4-ylene-(3-propionic acid) of formula (B), the reaction affords the corresponding alkyl ester of 7,7,8,8-tetracyanoquinodimethane-2,5-ylene-(3-propionic acid). In the former case, the product, when esterified, gives the latter product. The esterification is conducted by a known method, for example, by converting the former product to an acid chloride with thionyl chloride or the like and reacting the resulting product with an alcohol. The esterification can be effected also during the oxidation reaction by carrying out the oxidation reaction in the presence of an alcohol.

It will be noted that 2,5-bis(dicyanomethylene)cyclohexane-1,4-ylene-(3-propionic acid) or an ester thereof represented by formula (B) and serving as the starting material for the compound of formula (A) can be prepared, for example, by the following overall process. A dialkyl ester of succinylsuccinic acid represented by the formula

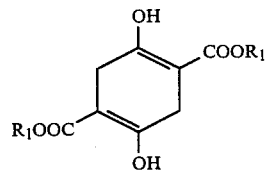

wherein $R_1$ is alkyl is reacted with acrylic acid or an alkyl ester of acrylic acid, or a mixture of such acid and ester, or a mixture of two different such esters, generically represented by the formula $$CH_2=CHCOOR$$

wherein R is the same as defined above, to obtain the starting material of the present invention, i.e. a cyclohexane-2,5-dione derivative of formula (II) above, wherein R and $R_1$ are as defined above, with the proviso that where a mixture of acrylic acid and an alkyl ester of acrylic acid, or a mixture of two different alkyl esters of acrylic acid, are used, each R individually is hydrogen or alkyl as aforesaid. The reaction is conducted usually in an organic solvent in the presence of a metallic alcoholate catalyst.

The cyclohexane-2,5-dione derivative of formula (II) is then heated in an aqueous medium, e.g. in the presence of a strong acid, such as hydrochloric acid, sulfuric acid, p-toluenesulfonic acid or a strong-acid type ion exchange resin, to give the cyclohexane-2,5-dione-1,4-ylene-(3-propionic acid) of the present invention represented by formula (I), which when esterified affords the corresponding ester of cyclohexane-2,5-dione-1,4-ylene-(3-propionic acid).

Subsequently, the cyclohexane-2,5-dione-1,4-ylene-(3-propionic acid) or the ester thereof of formula (I) according to the present invention is reacted with malondinitrile, giving 2,5-bis(dicyanomethylene)-cyclohexane-1,4-ylene-(3-propionic acid) or an ester thereof represented by formula (B) (cf. Acker et al, U.S. Pat. No. 3,115,506; Crawford, U.S. Pat. No. 4,229,364; and Obreiter, U.S. Pat. No. 3,526,497).

In the same way as the compounds of the present invention, the compounds of formula (A) are also useful as materials for producing polyesters, polyamides, polyurethanes, etc. and as intermediates for tetracyanoquinodimethane serving as organic semiconductors.

The present invention will be described in greater detail with reference to the following examples.

EXAMPLE 1

A 177.5 g (0.414 mole) quantity of cyclohexane-2,5-dione derivative represented by the formula

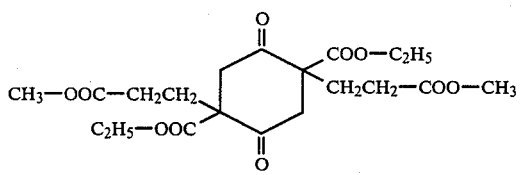

300 ml of water and 60 g of concentrated sulfuric acid were mixed together and refluxed for reaction. The reaction was continued for 120 hours while occasionally distilling off methanol and ethanol produced as by-products. On completion of the reaction, the remaining methanol and ethanol were distilled off, and the reaction mixture was cooled, whereby crystals were separated out. The crystals were filtered off to obtain 29.98 g of the desired product, i.e. cyclohexane-2,5-dione-1,4-ylene-(3-propionic acid).

The product was recrystallized from water. M.p. 192°–194° C. The data given below revealed that the compound obtained had the structure of:

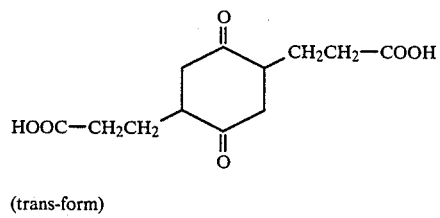

(trans-form)

IR: $\nu_{max}^{cm-1}$ 1700
NMR: $\delta_{CDCl_3}^{ppm}$ 1.3–3.0 (m, 14H)
Mass: m/e 256, 238, 220, 196, 178, 164, 150, 55

The above compound (25.6 g, 0.1 mole) was dissolved in 150 g of methanol and then esterified with stirring while adding thionyl chloride dropwise in 1.1 times the amount of the compound. After distilling off the solvent from the reaction mixture, the residue was recrystallized from methanol, giving 19.9 g of colorless needlelike crystals (yield 70%), i.e. cyclohexane-2,5-dione-1,4-ylene-(3-methyl propionate).

The crystals had a melting point of 112°–113° C.

The data given below revealed that the compound obtained had the structure of:

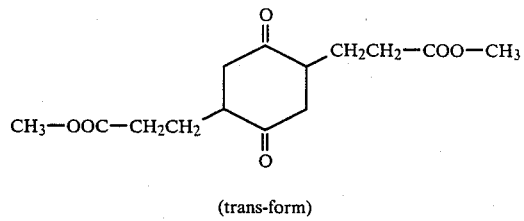

(trans-form)

IR: $\nu_{kBr}^{cm-1}$ 1730, 1700, 1185, 1165
NMR: $\delta_{CDCl_3}^{ppm}$ 3.72 (s, 6H), 1.3–3.0 (m, 14H)
Mass: m/e 284, 252, 221, 220, 178

When the same procedure as above was repeated using ehtanol in place of methanol, the compound obtained was found to have the following structure:

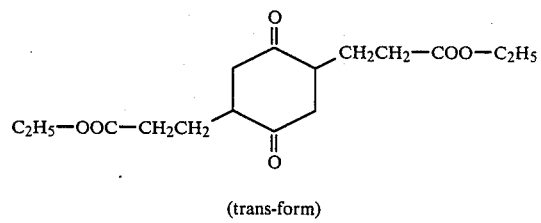

(trans-form)

M.p. 81°–82° C.
IR: $\nu_{kBr}^{cm-1}$ 1730, 1700
NMR: $\delta_{CDCl_3}^{ppm}$ 1.25 (t, J=7 Hz 6H), 4.15 (q, J—7 Hz 4H)
Mass: m/e 313, 312 (M+), 266, 221, 220, 178

EXAMPLES 2-3

The same procedure as in Example 1 was repeated except that the concentrated sulfuric acid was replaced by hydrochloric acid (Example 2) or by a strong acid-type ion exchange resin (Example 3), whereby the same result as above was obtained.

EXAMPLE 4

A 177.5 g (0.414 mole) quantity of cyclohexane-2,5-dione derivative represented by the formula

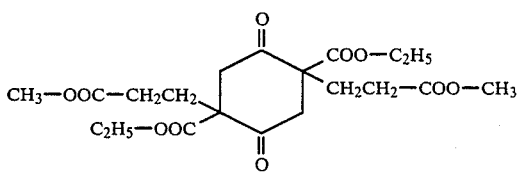

was admixed with 800 ml of water in an autoclave and reacted at 150° C. for 2 hours. On completion of the reaction, methanol and ethanol produced as by-products were distilled off, and the reaction mixture was cooled, whereby crystals were separated out. The crystals were filtered off to obtain 30.20 g of the desired product.

The product was recrystallized from water. M.p. 192°–194° C.

The data given below revealed that the compound obtained had the structure of:

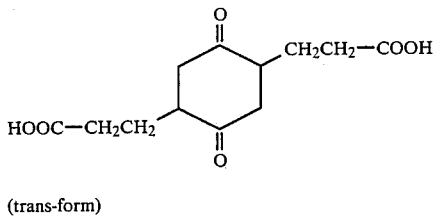

(trans-form)

IR: $\nu_{kBr}^{cm^{-1}}$ 1700
NMR: $\delta_{CDCl_3}^{ppm}$ 1.3–3.0 (m, 14H)
Mass: m/e 256, 238, 220, 196, 178, 164, 150, 55

The above compound (25.6 g, 0.1 mole) was dissolved in 150 g of methanol and then esterified with stirring while adding thionyl chloride in 1.1 times the amount of the compound dropwise to the solution. After distilling off the solvent, the residue was recrystallized from methanol, giving 19.9 g of colorless needlelike crystals (yield 70%).

The crystals had a melting point of 112°–113° C.

The compound obtained had the same structure as the corresponding compound prepared in Example 1 as shown below.

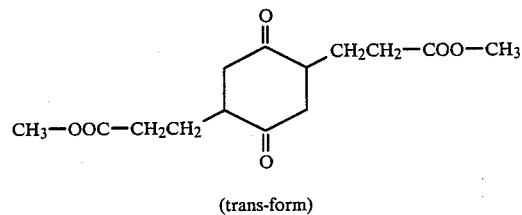

(trans-form)

EXAMPLE 5

Preparation of cyclohexane-2,5-dione derivative

[starting material of Example 1]

A 128.13 g quantity (0.5 mole) of diethyl succinylsuccinate, 112.4 g (1.3 moles) of methyl acrylate, 2.18 g (0.04 mole) of sodium methylate and 700 ml of methanol were mixed together in a reactor, the air within the reactor was replaced by argon, and the mixture was reacted for 15 hours with refluxing. The methanol was then distilled off at a reduced pressure, and a small amount of water containing benzene was added to the residue. The benzene layer was separated off, dried and then distilled in a vacuum, giving 181.97 g of yellowish brown oil (cyclohexane-2,5-dione derivative used in Example 1).

EXAMPLE 6

Preparation of tetracyanoquinodimethane derivative: 7,7,8,8-tetracyanoquinodimethane-2,5-ylene-(3-propionic acid)

[Use of compound produced in Example 1]

(a) A 1.28 g (5 mmoles) quantity of the cyclohexane-2,5-dione-1,4-ylene-(3-propionic acid) prepared per Example 1 was dissolved in 30 ml of water and then neutralized with an equivalent of sodium hydrogen carbonate. With addition of 0.66 g (10 mmoles) of malondinitrile and 0.1 g of β-alanine, the mixture was heated in a water bath for 2 hours, cooled and thereafter acidified with dilute hydrochloric acid. The crystals separating out were filtered off, washed and dried, giving 0.86 g of 2,5-bis(dicyanomethylene)cyclohexane-1,4-ylene-(3-propionic acid).

(b) The 0.86 g quantity of 2,5-bis(dicyanomethylene)cyclohexane-1,4-ylene-(3-propionic acid) obtained in (a) was dissolved in methanol. The solution was stirred at 10° C. for 2 hours with addition of 3.1 g of thionyl chloride. The resulting crystals were filtered off, washed and dried, giving 0.83 g of 2,5-bis(dicyanomethylene)cyclohexane-1,4-ylene-(3-propionic acid)-methyl ester.

(c) A 0.57 g quantity of the methyl ester of 2,5-bis(dicyanomethylene)cyclohexane-1,4-ylene-(3-propionic acid) obtained in (b) was suspended in 50 ml of acetonitrile. In an argon atmosphere, the suspension was stirred for 1 hour with addition of 0.6 g of N-bromosuccinimide. The mixture was cooled and then stirred for 2 hours with addition of 0.9 g of pyridine while maintaining the mixture at a temperature of up to 10° C. Water (30 ml) was added to the reaction mixture. The precipitate separating out was filtered off, washed with water and dried to obtain 0.51 g of the desired product. The yield was 90% based on the 2,5-bis(dicyanomethylene)cyclohexane-1,4-ylene-(3-propionic acid)methyl ester.

The compound had the following characteristic values and was identified as the methyl ester of 7,7,8,8-tetracyanoquinodimethane-2,5-ylene-(3-propionic acid).

M.p. 167°–168° C.
IR: $\nu_{kBr}^{cm^{-1}}$ 3050, 2960, 2215, 1740, 1550, 1515, 1200, 1175, 915, 900
NMR: $\delta_{CDCl_3\text{-}DMSO}^{ppm}$ 2.81 (4H T), 3.66 (6H S)
Mass: m/e 376, 345, 344, 317, 303, 259, 258(B), 257

EXAMPLE 7

7,7,8,8-Tetracyanoquinodimethane-2,5-ylene-(3-propionic acid) was obtained in a yield of 80% in the same manner as in Example 6 except that 2,5-bis(dicyanomethylene)cyclohexane-1,4-ylene-(3-propionic acid) was used in place of the methyl ester of 2,5-bis(dicyanomethylene)cyclohexane-1,4-ylene-(3-propionic acid).

EXAMPLES 8–9

Ethyl ester or n-propyl ester of 7,7,8,8-tetracyanoquinodimethane-2,5-ylene-(3-propionic acid) was prepared in the same manner as in Example 6 with the exception of using the ethyl ester or n-propyl ester of 2,5-bis(dicyanomethylene)cyclohexane-1,4-ylene-(3-propionic acid) in place of the methyl ester thereof.

EXAMPLE 10

Preparation of polyester resin

[Use of compound produced in Example 1]

A 284 g quantity (1.0 mole) of cyclohexane-2,5-dione-1,4-ylene-(3-methyl propionate), a 93 g quantity (1.5 mole) of ethylene glycol and a 0.12 g quantity ($5 \times 10^{-4}$ mole) of tin dibutyl oxide were placed into a reactor and subjected to esterification reaction for 3 hours while expelling methanol, as a by-product. Subsequently, with the addition of a 0.12 g quantity of tin dibutyl oxide, the reaction mixture was subjected to a condensation reaction for 2 hours at 240°–280° C. while expelling ethylene glycol under a vacuum of 1 mm Hg, giving a polyester, acid value 0.92, Tg 69° C., average molecular weight 1800.

EXAMPLE 11

Preparation of polyurethane resin

[Use of compound produced in Example 1]

A 100 g quantity (molecular weight 2100) of polyesterpolyol prepared in the same manner as in Example 10 where the molar ratio of cyclohexane-2,5-dione-1,4-ylene-(3-methyl propionate) to ethylene glycol was 1 to 1.3, a 181 g quantity of toluene, a 181 g quantity of methyl isobutyl ketone and 20 parts of neopentyl hydroxy pivalate were placed into a reactor and formed into a homogeneous solution. With the addition of 35.5 parts of diphenylmethane diisocyanate and 0.05 part of tin dibutyl dilaurate, the reaction mixture was reacted for 10 hours at 75°–80° C., giving a polyurethane, average molecular weight 25000.

What is claimed is:

1. A cyclohexane-2,5-dione-1,4-ylene-bis(-3-propionic acid) derivative represented by the formula

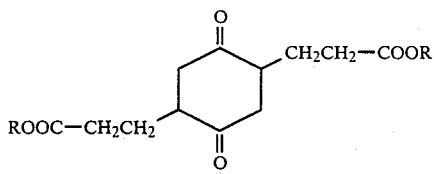

wherein R is hydrogen or alkyl having 1 to 10 carbon atoms.

2. Derivative of claim 1 wherein R is hydrogen.
3. Derivative of claim 1 wherein R is methyl.
4. Derivative of claim 1 wherein R is ethyl.
5. A cyclohexane-2,5-dione-1,4-ylene-bis(-3-propionic acid) derivative represented by the formula

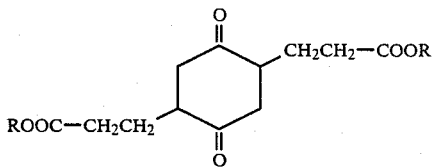

wherein R is hydrogen, methyl or ethyl.

* * * * *